(12) United States Patent
Reinboth et al.

(10) Patent No.: US 11,806,463 B2
(45) Date of Patent: Nov. 7, 2023

(54) COLLECTING UNIT FOR MEDICAL SUCTIONS WITH A FOLDED BAG

(71) Applicant: Drägerwerk AG & Co. KGaA, Lübeck (DE)

(72) Inventors: Thomas Reinboth, Lübeck (DE); Benjamin Fleitmann, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 328 days.

(21) Appl. No.: 17/091,227

(22) Filed: Nov. 6, 2020

(65) Prior Publication Data

US 2021/0138122 A1    May 13, 2021

(30) Foreign Application Priority Data

Nov. 7, 2019   (DE) ..................... 10 2019 007 716.4

(51) Int. Cl.
*A61M 1/00*   (2006.01)

(52) U.S. Cl.
CPC ............ *A61M 1/604* (2021.05); *A61M 1/602* (2021.05); *A61M 2207/00* (2013.01)

(58) Field of Classification Search
CPC .. A61M 1/604; A61M 1/602; A61M 2207/00; A61M 1/784
See application file for complete search history.

(56) References Cited

U.S. PATENT DOCUMENTS

| | | | |
|---|---|---|---|
| 3,745,999 A | | 7/1973 | Deaton |
| 4,013,076 A | * | 3/1977 | Puderbaugh .......... A61M 1/604 604/320 |
| 4,516,973 A | | 5/1985 | Telang |
| 4,583,972 A | * | 4/1986 | Hunter, III ............ A61M 1/684 604/75 |
| 4,981,473 A | * | 1/1991 | Rosenblatt ............ A61M 1/684 600/573 |
| 5,671,861 A | | 9/1997 | Hall et al. |
| 2008/0061064 A1 | * | 3/2008 | Michaels ............... A61M 1/882 220/495.06 |
| 2009/0292263 A1 | * | 11/2009 | Hudspeth ............... A61M 1/984 604/313 |
| 2010/0130957 A1 | * | 5/2010 | Smisson, III ....... A61M 1/3627 604/408 |

(Continued)

FOREIGN PATENT DOCUMENTS

| | | |
|---|---|---|
| CN | 101896218 A | 11/2010 |
| DE | 2826650 A1 | 12/1979 |

(Continued)

*Primary Examiner* — Susan S Su
*Assistant Examiner* — Eric Rassavong
(74) *Attorney, Agent, or Firm* — McGlew and Tuttle, P.C.

(57) ABSTRACT

A collecting unit, which receives secretion from a patient. The collecting unit comprises a cover (2) and a bag (3), which is mechanically connected to the cover (2). The bag (3) can be converted from a folded state, in which a portion of the bag (3) is folded about a fold axis (FA), into an unfolded state. Two overlapping overlap areas (3.1, 3.2) of the bag (3) that have each a connection area (VB.1, VB.2), are formed in the folded state. These connection areas (VB.1, VB.2) are detachably connected to one another, and preferably in a positively connected. The fold axis (FA) forms a common edge of the two overlap areas (3.1, 3.2).

7 Claims, 6 Drawing Sheets

(56) References Cited

U.S. PATENT DOCUMENTS

| | | | |
|---|---|---|---|
| 2014/0276492 A1* | 9/2014 | Pratt | A61M 1/98 604/319 |
| 2017/0106127 A1* | 4/2017 | Chang | A61M 1/604 |
| 2018/0318474 A1* | 11/2018 | Breitweiser | A61M 27/00 |
| 2021/0100709 A1* | 4/2021 | Begg | A61G 12/001 |

FOREIGN PATENT DOCUMENTS

| | | | |
|---|---|---|---|
| DE | 69916991 T2 | 5/2005 | |
| EP | 0040427 A1 | 11/1981 | |
| EP | 0072738 A1 | 2/1983 | |
| EP | 0669139 A1 | 8/1995 | |
| EP | 1642603 A1 | 4/2006 | |
| EP | 1984043 B1 | 12/2014 | |
| EP | 1225930 B2 | 10/2016 | |
| WO | 0124846 A1 | 4/2001 | |
| WO | 2007093670 A1 | 8/2007 | |
| WO | 2009080265 A1 | 7/2009 | |
| WO | 2010105775 A2 | 9/2010 | |
| WO | 2019162572 A1 | 8/2019 | |
| WO | WO-2020022977 A1* | 1/2020 | A61M 1/604 |

* cited by examiner

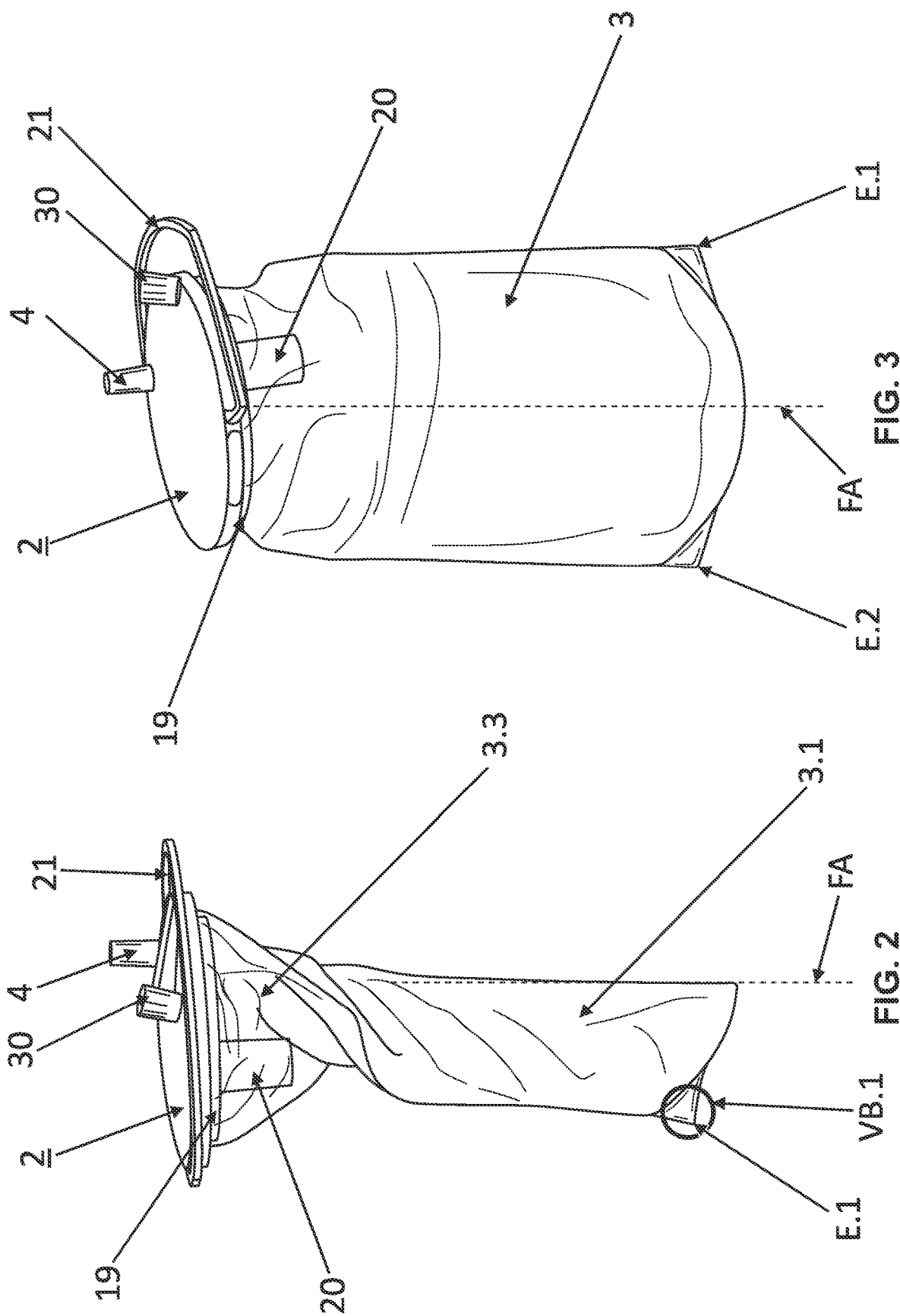

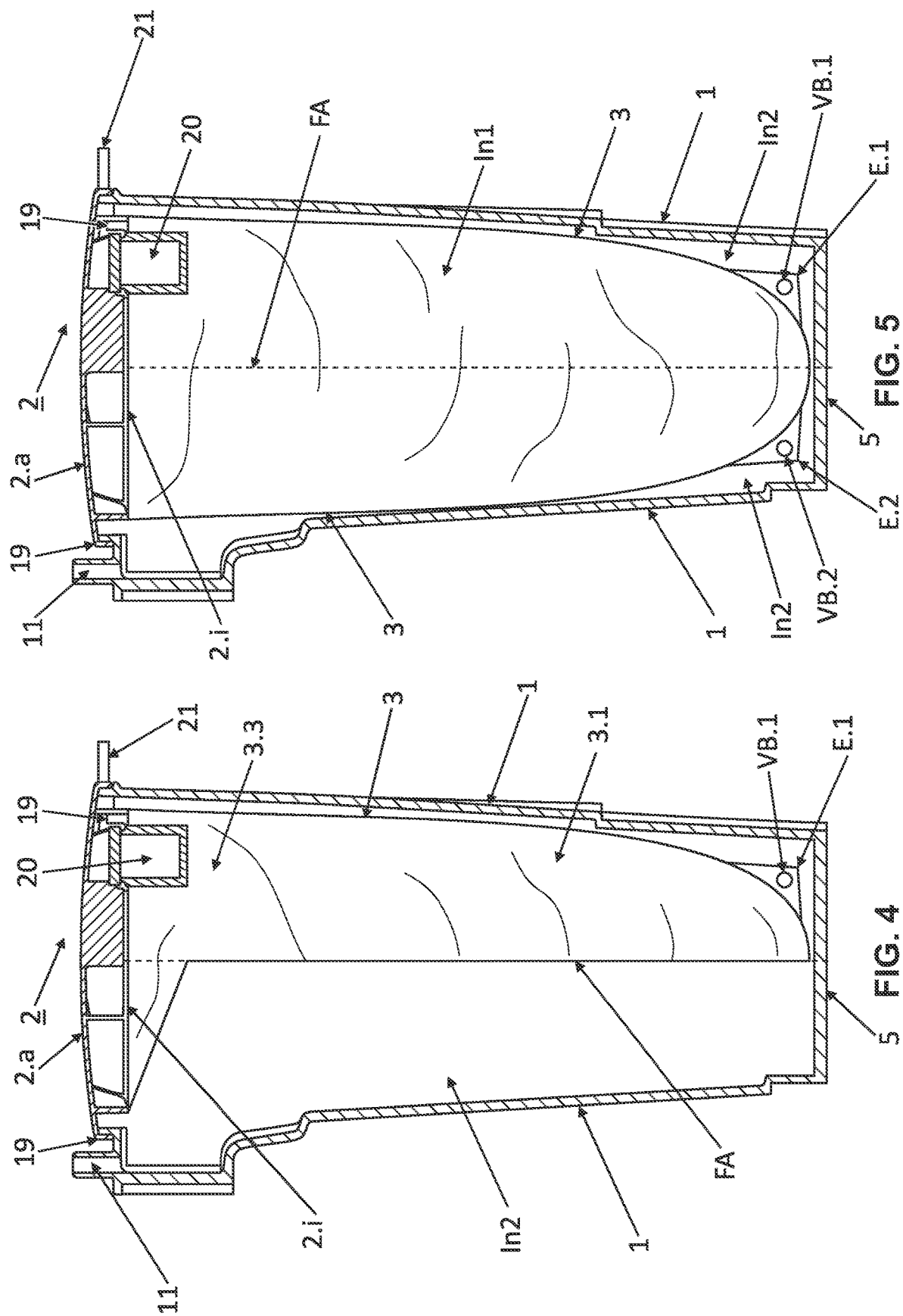

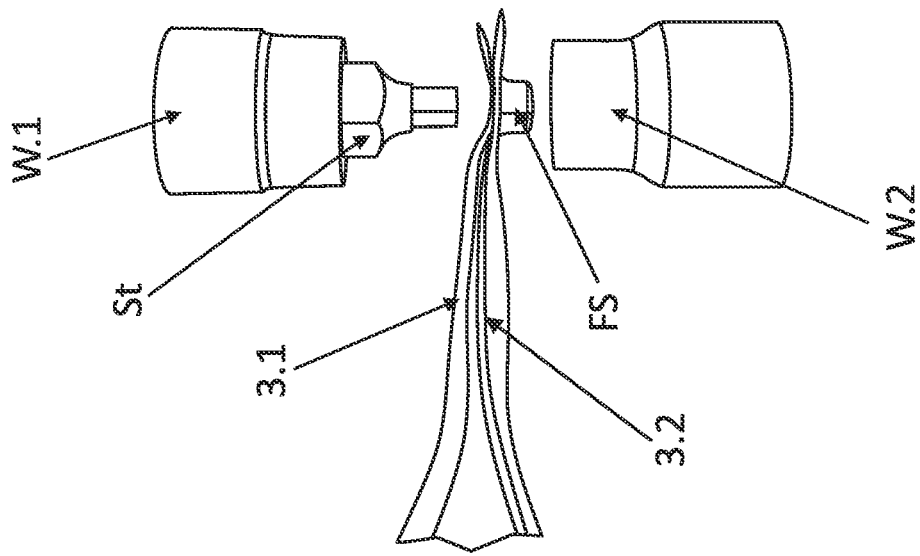
FIG. 10
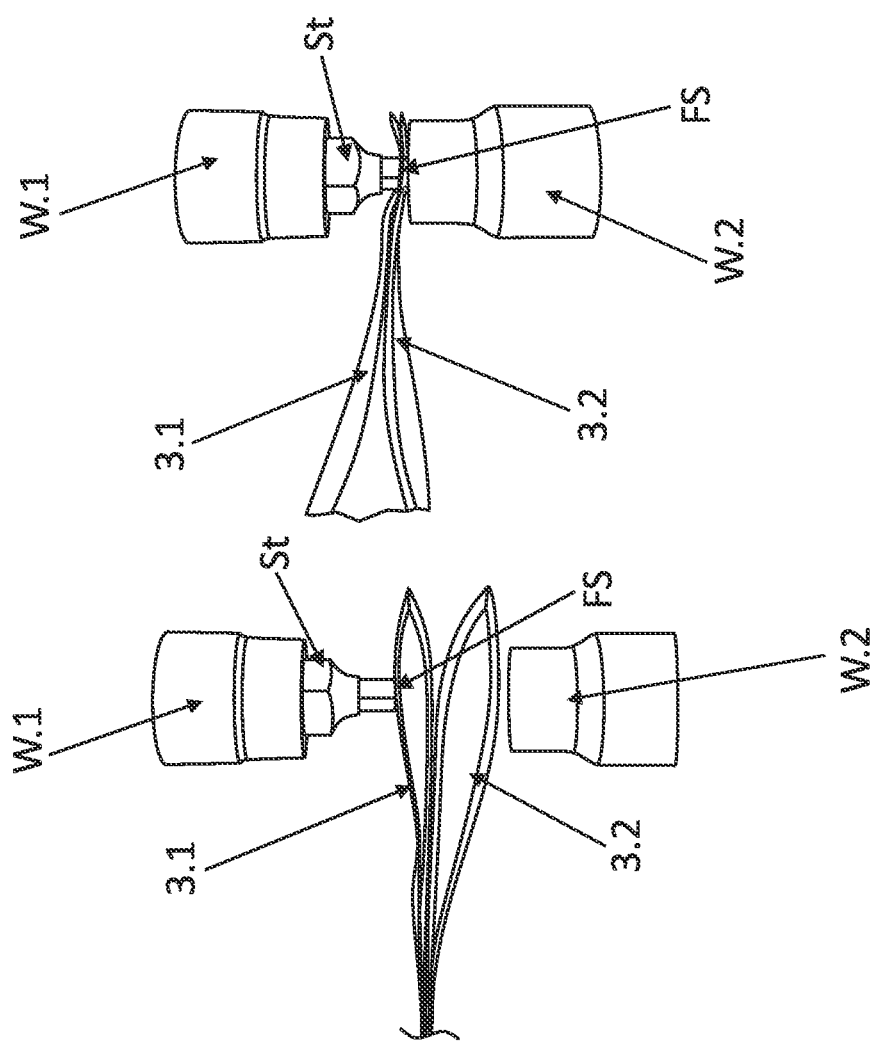
FIG. 9
FIG. 8

COLLECTING UNIT FOR MEDICAL SUCTIONS WITH A FOLDED BAG

CROSS REFERENCE TO RELATED APPLICATIONS

This application claims the benefit of priority under 35 U.S.C. § 119 of German Application 10 201 900 7716.4, filed Nov. 7, 2019, the entire contents of which are incorporated herein by reference.

TECHNICAL FIELD

The present invention pertains to a collecting unit for receiving secretion suctioned out of a patient.

TECHNICAL BACKGROUND

Such a collecting unit can be used as a component of a collecting device. This collecting device is connected to a patient-side coupling unit, on the one hand, and to a vacuum source, on the other hand, to suction secretion out of a patient, for example, in a hospital. A vacuum is generated in an interior of the collecting device, and consequently secretion is suctioned out and suctioned into the collecting unit and received by same. The collecting unit with the secretion is disposed of.

A variety of such collecting units have become known.

A collecting device with a container (collection container 1), with a cover (4) and a bag (suction bag 3) attached to the cover is described in EP 1225930 B2. A vacuum connector (2) is fastened to the container (1) via a conduit (10). A vacuum source is able to generate a vacuum in the container (1) via the conduit (10) and another conduit (7). A filter (6) is mounted on the inner side of the cover (4) and on the end of the conduit (7), which end points towards the container (3). In case this filter (6) comes into contact with a liquid, the filter (6) seals the conduit (7).

WO 2007093670 A1 and EP 1984043 B1 show a collecting device (suction bag arrangement) that is able to receive secretion from a patient. This suction device comprises a cover (110, 310), an outer container (suction canister 320), an expandable bag (suction bag 100, 300, 500), a patient-side connector (312) and a device-side connector (underpressure-vacuum-connector 322). The expandable bag (100, 300, 500) is attached to the cover (110, 310) and is folded such that both the length and the width of the bag (100, 300, 500) are cut in half compared to when the bag is unfolded. Two overlapping areas of the bag (100, 300, 500) are connected to one another by means of fastening elements (330, 332).

SUMMARY

A basic object of the present invention is to provide a collecting unit for receiving secretion that is suctioned out of a patient, which collecting unit can be more easily inserted into a container than prior-art collecting units and moreover can be more easily manufactured.

The collecting unit according to the present invention is able to receive secretion, which has been suctioned out of a patient.

The collecting unit comprises a cover and a bag. The bag is mechanically connected to the cover. The bag and the cover together enclose a collecting unit interior. The collecting unit is able to receive secretion in this collecting unit interior.

The bag has at least one fold axis, and preferably precisely one fold axis. The bag can be converted from a folded state into an unfolded state. In the folded state, the bag is partially folded about the fold axis or about at least one fold axis.

When the bag is in the folded state and is folded about the fold axis or one fold axis, the collecting unit according to the present invention has the following properties:

Two overlapping overlap areas of the bag are formed. Each of these overlap areas has a respective connection area.

The two connection areas are detachably connected to one another.

The fold axis or one fold axis of the bag forms a common edge of these two overlap areas.

At least when the bag is in the folded state, the collecting unit according to the present invention can be inserted into a container, preferably into a rigid container, before use. The bag, which is folded along the fold axis or along one fold axis, protrudes at least partially into this container.

Because the bag is folded during the insertion into the container, the bag can be inserted more easily and more rapidly into the container than if it were not folded. The collecting unit according to the present invention may, in many cases, be inserted into the container by a single movement and has only to be held at the cover. The risk is low that the folded bag remains attached to the container during insertion and has to be moved into the container by means of a separate movement or the bag is located between the cover and the container or outside of the container even after the insertion of the collecting unit into the container. Thanks to the folding along the fold axis, the collecting unit according to the present invention can be made ready for use with less time required than in case of other collecting units.

As a rule, the collecting unit according to the present invention is manufactured at one location and is transported to a location of use, for example, in a hospital. Because the bag is folded along the fold axis, the collecting unit takes up less space during the transport than if the bag were not folded. The fold axis or each fold axis determines where the bag is folded and in many cases ensures that the collecting unit can be inserted into a container. The need to fold the bag "somehow" in order to save space by folding is avoided.

The two connection areas of the two overlap areas are detachably connected to each other. The bag does not unfold before use because the two overlap areas are connected to one another. Unfolding of the bag before use is, as a rule, undesired.

Since the connection is detachable, it is made possible that the connection between the two overlap areas is severed during use. The bag unfolds in the container during use, and the unfolded bag can receive more secretion than the folded bag.

According to the present invention, the two connection areas are detachably connected to each other and preferably with a form fit connection. When the bag is in the folded state, at least one of the following two states occurs: The connection area of the one overlap area is completely or at least partially wrapped (wound) around the connection area of the other overlap area. Or the connection area of the one overlap area is pressed into the connection area of the other overlap area to provide a form fit press connection (pressed form fit connection).

The detachable connection between the two overlap areas is established before use, for example, by means of clinching (press joining), and can be severed again during use, for example, because a vacuum is applied to the bag and expands same.

This embodiment, in which one connection area is wrapped (wound) around the other connection area or is pressed into same, does not require a separate connection element, especially no adhesive strips, in order to connect the two overlap areas to one another. A separate process step is necessary to provide the connection element in order to attach such a connection element during the manufacture of the bag. The connection element must be disposed of after use. Moreover, there is a risk that the connection element adheres too strongly to the bag and therefore the bag tears during the unfolding and a tear forms, through which secretion can run out. Or the connection element adheres too weakly to the bag and tears off prematurely, so that the bag unfolds too early.

The two alternatives, namely that one connection area is wrapped (wound) around the other connection area and that one connection area is pressed into the other connection area, can be combined. For example, a first part of one connection area is wrapped (wound) around a first part of the other connection area. A second part of the one connection area is pressed into a second part of the other connection area. The two parts are separated from one another in space, preferably arranged at a spaced location from one another.

According to the present invention, the two overlap areas are detachably connected to one another without an additional component, especially without a separate fastening element. Consumable material, namely a separate fastening element, is saved as a result. The risk that the bag is not able to unfold correctly or that the bag is damaged by a separate fastening element during the unfolding is reduced in many cases. In addition, an additional step in the case of establishing the detachable connection is in many cases eliminated.

The detachable connection between the connection areas is preferably a form fit connection. This creates an integral connection that avoids e.g., a bonding or a soldering. Such bonding or a soldering may lead to the bag tearing during the unfolding.

The bag is preferably folded along precisely one single fold axis. This fold axis preferably extends along a symmetry axis of the bag. A dimension of the bag in a direction parallel to the fold axis is not greater when the bag is unfolded—at least as long as the ambient pressure remains identical. As a result, the bag has to unfold only along one axis and not along a plurality of axes. The risk that the bag does not unfold entirely in the container during use and is not able to receive the maximum possible quantity of secretion as a result, is lower than in the case of other collecting units with folded bags thanks to the present invention.

The collecting unit according to the present invention preferably has the following property: At least if the ambient pressure acting on the bag remains identical during the unfolding, the maximum dimension of the bag in a direction parallel to the fold axis also remains identical, when the bag is converted from the folded state into the unfolded state. This property facilitates the handling of the collecting unit according to the present invention, especially when this collecting unit is inserted into a container and unfolds there.

According to the present invention, two overlap areas are formed, when a portion of the bag is folded about the fold axis. In a preferred embodiment, these two overlap areas have the same maximum dimension in a direction at right angles to the precisely one fold axis. This embodiment makes it possible to utilize the available space at best.

According to the present invention, the bag can be converted from a folded state into an unfolded state. The only fold axis or a fold axis preferably runs centrally through the bag when the bag is in the unfolded state. This embodiment leads to an especially small dimension of the folded bag in a direction at right angles to the fold axis. Available space can be utilized quite well, for example, during the transport of the collecting unit. In a preferred embodiment, the bag in the unfolded state is symmetrical in relation to a plane of symmetry. The precisely one fold axis is located in this plane of symmetry.

In a preferred embodiment, the fold axis or a fold axis runs centrally through the bag. Hence, the two overlap areas preferably have approximately the same dimension in a direction at right angles to the fold axis. As a result, a more simple construction is made possible than when there would be overlap areas of different dimensions. The folded bag takes up less space than in the case of other possible embodiments.

The bag is preferably expandable and the cover is rigid. As a result, the collecting unit is able to receive more secretion than if the bag were also rigid. The rigid cover increases the stability of the collecting unit and makes it easier to mount or to grasp the collecting unit in a container.

According to the present invention, the two overlap areas are detachably connected to one another in the two connection areas. During use, this connection between the overlap areas is severed on its own when the bag unfolds.

Before the unfolding the two connection areas preferably have the maximum possible distance from the fold axis and each adjoin an edge of the bag. A greatest possible leverage develops. As a result, only the lowest possible force is needed to sever the detachable connection, compared with a different positioning of the two connection areas. In one embodiment, each overlap area has a respective corner, which is arranged at a spaced location from the cover and from the fold axis. The connection area of an overlap area adjoins the corner of this overlap area.

The bag is preferably made of a flexible material. As a result, the folded bag takes up less space during a transport to the location of use than if it were to be made of a different material. The bag can be folded without a special fold area made of a different material being necessary.

The collecting unit according to the present invention is preferably a component of a collecting device, which comprises, moreover, a container with a bottom. The container is preferably made of a rigid material. The collecting unit may be connected to the container such that the bag protrudes into the container. When the bag is freely attached to the cover and the cover is placed onto the container, the fold axis or each fold axis, about which the bag is folded, is ideally at right angles to the cover and at right angles to the bottom. The folded bag preferably reaches from the cover to the bottom of the container and especially preferably touches the bottom. The bag preferably has to be unfolded only about a single axis, namely about the fold axis, during use. The bag does not have to expand to the bottom or along the bottom during unfolding. The unfolding is faster and takes place with a higher operational safety than if the bag had to unfold about two different axes. The space in the container is utilized optimally.

An embodiment of the present invention pertains to a collecting device comprising a collecting unit according to the present invention and a container, which can preferably be reused. The container carries the cover of the collecting unit. The bag of the collecting unit is attached to the cover and protrudes into the container. The bag can preferably unfold while it is attached to the cover and protrudes into the container. The cover and the container together enclose a container interior.

Various processes are possible to manufacture the collecting unit according to the present invention. A preferred manufacturing process comprises the following steps:

The cover is manufactured.

The bag is manufactured, especially such that it is in the unfolded state after the manufacturing.

A portion of the bag is folded along the fold axis or along each fold axis. The bag is converted into the folded state as a result. Due to the folding, the two overlapping overlap areas are formed.

The two connection areas of the two overlap areas are detachably connected to one another.

In this case, the one connection area is at least partially wrapped (wound) around the other connection area. Or the one connection area is pressed into the other connection area.

The bag is mechanically connected to the cover, preferably with a circumferential projection at the cover.

This embodiment of the manufacturing process makes it easier to manufacture a large number of collecting units according to the present invention. The still unfolded bags can be manufactured from a tube, e.g., by a respective segment being cut off from the tube, the segment being sealed at one end by a preferred connection in substance and the bag being manufactured from this sealed segment. The cover, which may be rigid, does not impair the manufacture of the bag. The cover and the bag can be manufactured separately from one another, even in large quantities, which makes the manufacture of special casting molds and plants, e.g., for joining connection economical.

A collecting unit according to the present invention can be used to receive secretion that has been suctioned out of a patient in different manners. A preferred process to use the collecting unit comprises the following steps:

The collecting unit according to the present invention is detachably connected to a container, for example, inserted into the container. After this connection, the bag protrudes into the container. The bag is in the folded state in this case. A portion of the bag is folded along the fold axis.

The container and the cover of the collecting unit connected to the container together enclose a container interior, namely preferably in a fluid-tight manner (with a fluid tight connection enclosure). This container interior comprises the collecting unit interior of the collecting unit.

A patient-side fluidic connection is established between a patient-side coupling unit and the collecting unit interior.

A device-side fluidic connection is established between a vacuum source and the container.

The vacuum source generates a vacuum, which propagates in the container interior thanks to the device-side fluidic connection.

The vacuum generated has the effect that the container which is located in the container interior expands.

Because of the expansion of the bag, the connection between the two overlap areas of the bag is severed.

The bag is converted into the unloaded state due to the vacuum.

Because of the vacuum, secretion is suctioned into the unfolded bag through the patient-side fluidic connection.

The two steps, that the bag unfolds and that secretion is suctioned into the bag, may overlap in time.

This preferred process to use the collecting unit makes it possible to insert the folded bag into the container, which is often simpler than using an unfolded bag. The embodiment further leads to the bag being unfolded on its own, namely because of the vacuum applied and while the bag is enclosed by the cover and by the container. It is possible but not necessary to unfold the bag manually or by using a special tool thanks to the configuration. Furthermore, it is not necessary to blow a fluid into the folded bag in order to unfold it.

The present invention will be described below based on an exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the Drawings:

FIG. 2 is a perspective view showing a collecting unit with the bag folded along the fold axis;

FIG. 3 is a perspective view showing the collecting unit from FIG. 2 with the bag unfolded;

FIG. 4 is a sectional view showing the collecting device with the bag folded along the fold axis;

FIG. 5 is a sectional view showing the collecting device from FIG. 4 with the bag unfolded;

FIG. 8 is a view showing one of three consecutive steps during the manufacture of a bag of the collecting unit;

FIG. 9 is a view showing another of three consecutive steps during the manufacture of a bag of the collecting unit; and FIG. 10 is a view showing another of three consecutive steps during the manufacture of a bag of the collecting unit.

DESCRIPTION OF PREFERRED EMBODIMENTS

Figure 1:
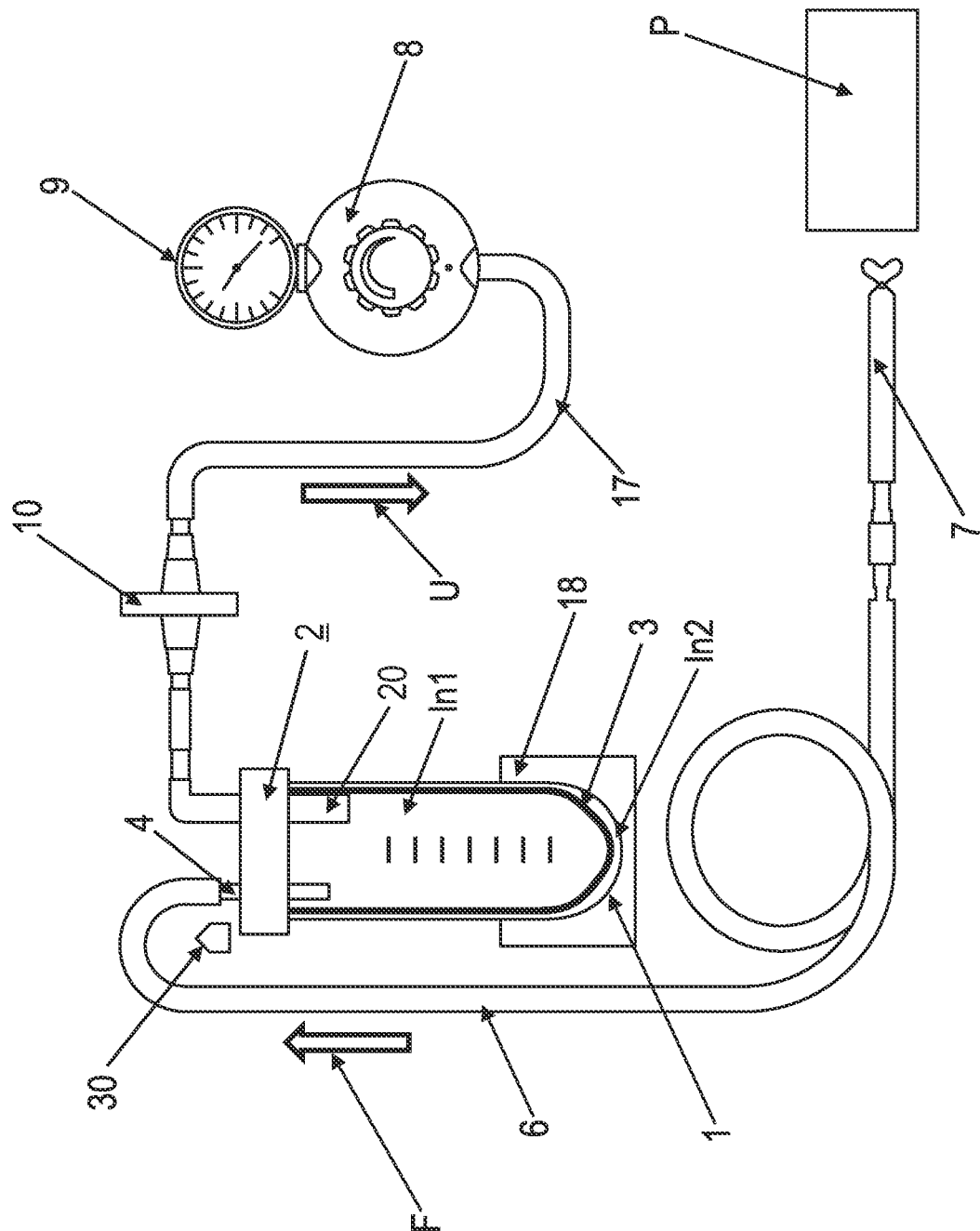
FIG. 1 is a schematic view of a suction system which comprises a collecting device, a patient-side coupling unit and a vacuum source.

Referring to the drawings, FIG. 1 schematically shows a suction system that comprises a collecting device with a collecting unit according to the present invention. The suction system is temporarily connected to a patient P and is able to suction out and receive secretion S from the patient P.

The collecting unit of the exemplary embodiment comprises
a cover 2,
an expandable bag 3, which is fluid tightly attached to the cover 2,
a hollow patient-side connector 4, which is permanently and fluid tightly connected to the cover 2 and protrudes outwards, an overflow protection device 20, and a cap 30, with which the patient-side connector 4 can be reversibly closed from outside.

The cover 2 comprises an arched outer side 2.*a*, a flat inner side 2.*i* and a circumferential projection 19 that is fastened to the flat inner side 2.*i* and is preferably circular or elliptical. The terms "inside" and "outside" refer to the space which is enclosed by the bag 3 and by the cover 2. The cover 2 is made of solid or flexible plastic. One or two grips 21 are preferably arranged laterally on the cover 2 in order to be able to open and carry the cover 2.

The bag 3 is expandable, preferably transparent and is preferably guided about the circumferential projection 19 under tension and in this manner is fastened to the cover 2 in a fluid-tight manner.

The collecting device comprises this collecting unit 2, 3, 4, 20, 30 and furthermore a container 1 with a bottom 5, wherein the container 1 is permanently connected to a foot 18, which stands on a surface, or is detachably placed onto such a foot 18, a suction tube 6, which can be placed onto or into the patient-side connector 4 or be screwed into same, and a device-side connector 11 in a wall of the container 1.

The cover 2 is placed on the top onto the container 1 in a fluid-tight but detachable manner. The expandable bag 3 is attached to the cover 2 and protrudes into the container 1.

The suction system comprises the collecting device with the collecting unit according to the present invention and moreover a catheter 7, which is connected to the suction tube 6 in a fluid-tight manner and is used at the patient P, a vacuum source 8, which can be switched on and switched off, a pressure difference measuring device 9, which measures and displays the vacuum, which the vacuum source 8 has generated, in relation to the ambient pressure, a device-side tube 17, which connects the vacuum source 8 to the device-side connector 11 in a fluid-tight manner, and optionally a filter 10 in the tube 17, which prevents the secretion droplets from reaching the vacuum source 8.

The container 1 is made of solid plastic, is preferably transparent and can be used multiple times. The container 1 is cleaned after each use. The collecting unit 2, 3, 4, 20, 30 can be inserted into the container 1 and can be removed again from the container 1.

The cover 2 and the expandable bag 3 together enclose a collecting unit interior In1 in a fluid-tight manner. An additional interior In2, which encloses the collecting unit interior In1, is formed between the outer wall of the bag 3 and the inner wall of the container 1. The two interiors In1 and In2 together form a container interior In1, In2 that is enclosed by the container 1 and by the cover 2.

The patient-side connector 4 makes it possible to provide a patient-side fluidic connection between the outer side of the cover 2 and the collecting unit interior In1 in the bag 3. This patient-side fluidic connection passes through the cover 2.

The suction tube 6 can be placed or pushed onto or inserted into the patient-side connector 4 or even screwed into the patient-side connector 4. In case of the inserted or placed or screwed-in suction tube 6, the suction tube 6 encloses the patient-side connector 4 in a fluid-tight manner, or the patient-side connector 4 encloses the suction tube 6 in a fluid-tight manner. A patient-side fluidic connection can be established between the catheter 7 and the collecting unit interior In1. This patient-side fluidic connection passes through the suction tube 6, through the patient-side connector 4 and through a hole in the cover 2 to the collecting unit interior In1.

The cap 30 can then be placed onto the patient-side connector 4 when the suction tube 6 is pulled off or removed in a different way from the patient-side connector 4.

The device-side connector 11 makes it possible to establish a device-side fluidic connection between the outer side of the cover 2 and the additional interior In2. The device-side tube 17 can be placed onto the device-side connector 11.

FIG. 2 and FIG. 3 show the collecting unit with the cover 2 and with the bag 3 perspectively, wherein the bag 3 is fastened to the circumferential projection 19. Furthermore, the patient-side connector 4 and the cap 30 can be seen. Furthermore, the overflow protection device 20 in the form of a cylindrical sintered filter is shown. This sintered filter 20 is fastened to the inner side 2.*i* of the cover 2 and protrudes into the collecting unit interior In1. When rising liquid reaches the sintered filter 20 in the collecting unit interior In1, this sintered filter 20 swells up and prevents liquid from exiting the collecting unit interior In1 through a duct in the cover 2. This liquid therefore cannot reach the device-side connector 11.

When the bag 3 is attached freely to the cover 2, the bag 3 extends along a fold axis FA, which—in case of a freely attached bag 3—is at right angles to the inner side 2.I of the cover 2. When the cover 2 is placed onto the container 1 and the bag is freely attached to the placed-on cover 2, this fold axis FA is arranged approximately at right angles. The bag 3 at the cover 2 preferably reaches to the bottom 5 of the container 1.

The expansion along the fold axis FA is the greatest expansion of the bag 3. Before the bag 3 is inserted into the container 1, the bag is partially folded along this fold axis FA and hence is in the folded state. FIG. 2 shows the bag 3, which is partially folded along the fold axis FA and therefore is in a folded state. A first overlap area points towards the viewer. The second overlap area 3.2 is located behind the first overlap area 3.1, viewed in the viewing direction.

Both overlap areas 3.1, 3.2 have an approximately trapezoidal shape in the exemplary embodiment, wherein the fold axis FA forms the respective longest edge of these two trapezoids. A connection area VB.1 adjoins a corner E.1 of the first overlap area 3.1, which is arranged at a spaced location from the cover 2 and from the fold axis FA. The other overlap area 3.2 has a corner E.2, which is located behind the corner E.1 and which a connection area VB.2 of the second overlap area 3.2 adjoins.

The two overlap areas 3.1 and 3.2 pass over in a common connection area 3.3, which is connected to the cover 2 and preferably extends around the circumferential projection 19. The sintered filter 20 protrudes into this connection area 3.3.

The two overlap areas 3.1 and 3.2 of the folded bag 3 are detachably connected to one another in the two connection areas VB.1 and VB.2. For example, the connection area VB.1 of the first overlap area 3.1 is at least partially wrapped (wound) around the connection area VB.2 of the second overlap area 3.2 or vice versa. Or a part of the connection area VB.1 of the first overlap area 3.1 is pressed into the connection area VB.2 of the second overlap area 3.2 or vice versa. In the exemplary embodiment, the two connection areas VB.1 and VB.2 are exclusively connected to one another with a form fit connection without a special fastening element or a bonded connection or a thermal connection being used.

FIG. 3 shows the collecting unit from FIG. 2, wherein the bag 3 is unfolded and therefore is in an unfolded state. The bag 3 remains attached to the cover 2 during the conversion from the folded state into the unfolded state. The connection between the two connection areas VB.1 and VB.2 is severed because of the unfolding. The unfolded bag 3 is symmetrical to a plane of symmetry that is at right angles to the drawing plane of FIG. 3 and in which the single fold axis FA is located. The fold axis FA is thus arranged approximately centrally in the ideally unfolded bag 3. The unfolded bag 3 together with the cover 2 encloses the collecting unit interior In1. The situation that is shown in FIG. 3 is established during the operation, after the collecting unit 2, 3, 4, 30 has been inserted into the container 1. This container 1 is omitted in FIG. 3. The dimension of the bag 3 remains approximately constant during the unfolding in a direction parallel to the fold axis FA, and the dimension of the bag 3 in a direction at right angles to the fold axis FA is doubled.

FIG. 4 and FIG. 5 show a cross section through the collecting device according to the exemplary embodiment. The patient-side connector 4 is omitted. In FIG. 4, the bag 3 is folded partially along the fold axis FA, and the overlap area 3.1 points towards the viewer. In FIG. 5, the bag 3 is unfolded and together with the cover 2 encloses the collecting unit interior In1. The cover 2 is placed onto the container 1 and carries the bag 3. The bag 3 hangs in the container 1 and preferably reaches to the bottom 5 of the container 1. The fold axis FA, the two corners E.1 and E.2 as well as the two connection areas VB.1 and VB.2 of the bag 3 are shown.

In the example shown in FIG. 2 through FIG. 5, each connection area VB.1, VB.2 belongs to a respective triangular surface ("ears" of the unfolded bag 3), wherein in each triangular surface, two areas of the wall of the bag 3 overlap and the triangular surface provides practically no volume for receiving secretion even in the unfolded state of the bag 3. In this triangular surface, the connection areas VB.1, VB.2 take up the entire triangular surface or a part of the triangular surface.

Figure 6:
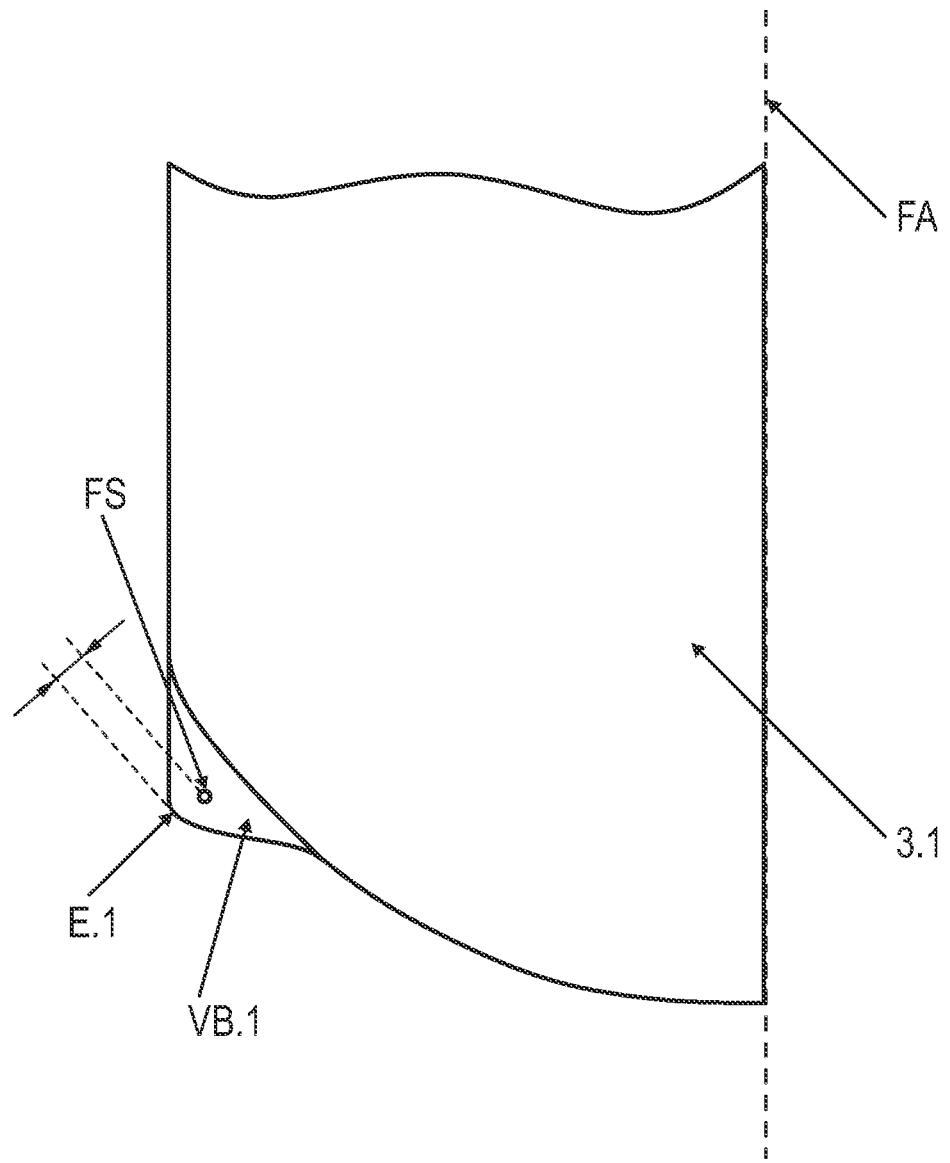
FIG. 6 is a schematic view showing a part of the overlap area of the folded bag.

FIG. 6 shows a lower part of the first overlap area 3.1. The approximately triangular connection area VB.1 as well as the corner E.1 are shown. At a joining point FS, a part of the connection area VB.1 is pressed into the corresponding connection area VB.2 of the second overlap area 3.2.

Figure 7:
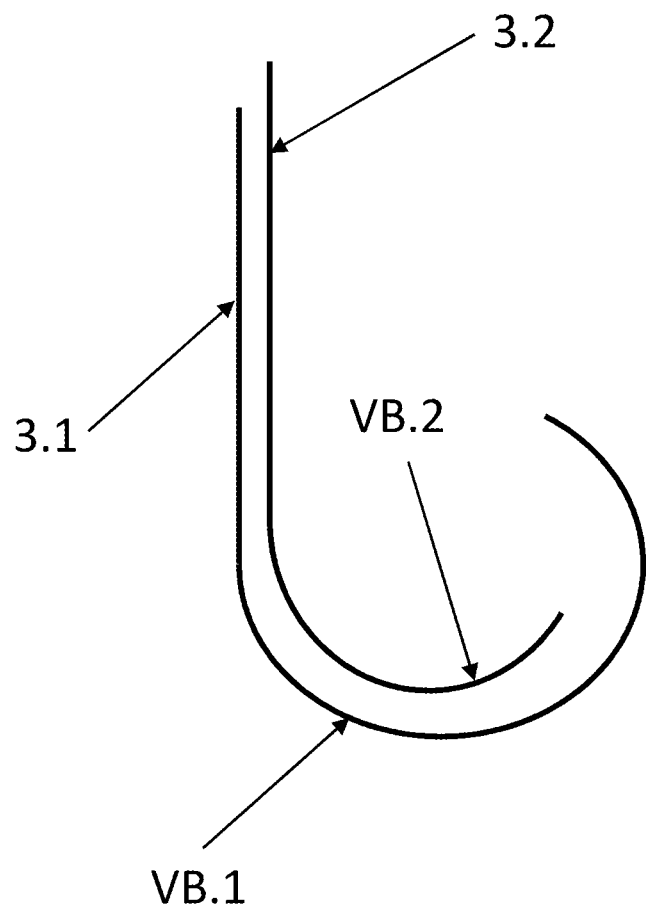
FIG. 7 is a schematic view showing an embodiment of a detachable connection of the two connection areas shown with a viewing direction that is perpendicular to that of FIGS. 4, 5 and 6.

FIG. 7 shows an example of a detachable connection of the two connection areas. In the example of FIG. 7 the connection area VB.1, is wrapped around the other connection area, in this case VB.2. The folded bag 3 is shown from the side, i.e., the viewing direction of FIG. 7 is perpendicular to that of FIGS. 4, 5 and 6.

FIG. 8 through FIG. 10 show, as examples, three situations which are achieved one after the other in a preferred process for manufacturing the folded bag 3 shown in FIGS. 2-4. The bag 3 is manufactured by a piece being cut off from a tube, not shown, and being sealed at a point by connection in substance. The bag 3 manufactured in this manner is folded along the single fold axis FA. The two overlap areas 3.1 and 3.2, which overlap and are not yet connected to one another, are placed between two tools W.1 and W.2. The tool W.1 has a plunger St, which can mesh with a corresponding recess in the tool W.2.

In the situation shown in FIG. 8, a space develops between the two tools W.1 and W.2, and the two connection areas VB.1 and VB.2 of the two overlap areas 3.1 and 3.2 are located in the space between the two tools W.1 and W.2. The two overlap areas 3.1 and 3.2 are preferably held under tension, while they are placed into a position between the two tools W.1 and W.2.

The two tools W.1 and W.2 are moved towards one another and the plunger St of the tool W.1 enters the corresponding recess in the tool W.2. The resulting situation is shown in FIG. 9. At the joining point FS, the first connection area VB.1 is pressed into the second connection area VB.2, so that four layers of the wall of the bag 3 overlap at this point. The joining connection is preferably established without heating the bag 3 or the plunger St.

The two tools W.1 and W.2 are again spaced apart from one another. The two overlap areas 3.1 and 3.2 are now detachably connected to one another in the joining point FS. FIG. 10 shows the resulting situation. The two overlap areas 3.1 and 3.2 are stripped off from the plunger St. The two overlap areas 3.1 and 3.2 are firmly connected to one another such that they are, as a rule, not separated from one another during a transport to a location of use.

The collecting unit of the exemplary embodiment is preferably manufactured as follows:

The cover 2 together with the circumferential projection 19 and the patient-side connector 2 is manufactured, namely preferably by casting, i.e., by a heated and thereby liquid plastic being filled into a casting mold and cured there and then preferably being freed from burrs and the like. In one embodiment, an arched outer cover part 2.a with the patient-side connector 4 and a flat inner cover part 2.i with the projection 19 are manufactured separately from one another and are then permanently connected to one another. In another embodiment, the entire cover 2 is manufactured in a single manufacturing step.

The sintered filter 20 is fastened to the flat inner side 2.i of the cover 2.

The bag 3 is manufactured, for example, by a piece being cut off from a tube, which extends along a fold axis FA, preferably with a bent cutting edge. An edge, which is at right angles to the fold axis FA, is welded, preferably the bent edge, which later forms the lower end of the bag 3. The not yet folded bag 3 is produced by the welding.

The bag 3 is folded along the single fold axis FA, so that two overlapping overlap areas 3.1 and 3.2 are provided.

These two overlap areas 3.1 and 3.2 are detachably connected to one another, for example, as illustrated by FIG. 8 through FIG. 10.

The folded bag 3 is pulled over the circumferential projection 19 at the cover 2 in the connection area 3.3, i.e., at the open end, and as a result is connected to the cover 2 in a fluid-tight manner. The collecting unit produced as a result appears, e.g., as shown in FIG. 2.

The collecting unit produced in this manner with the folded bag 3 is brought to a location of use, for example, in a hospital.

In a variant embodiment, the not yet folded bag is first pulled over the circumferential projection 19 at the cover 2, and the bag 3 is then folded along the fold axis FA.

Described below are what steps are carried out in order to use the collecting unit of the exemplary embodiment for receiving suctioned secretion, e.g., in a hospital.

The collecting unit with the cover 2 and with the bag 3 folded partially along the fold axis FA is brought to a location of use.

The cover 2 is placed onto the container 1, so that the folded bag 3 is attached to the cover 2 and protrudes into the container 1. The container 1 and the cover 2 enclose in a fluid-tight manner the container interior In1, In2, which consists of the collecting unit interior In1 in the bag 3 and the additional interior In2 between the bag 3 and the inner wall of the container 1. This situation is shown in FIG. 2.

The suction tube 6 is placed onto or inserted into the patient-side connector 4. As a result, a patient-side fluidic connection is established between the catheter 7 and the collecting unit interior In1.

If not already done before, the device-side tube 17 is placed onto the device-side connector 11. As a result, a device-side fluidic connection is established between the vacuum source 8 and the additional interior In2.

Up to now, the bag 3 has remained in the folded state. The vacuum source 8 is switched on and suctions air through the device-side connector 11 from the container interior In1, In2, which is enclosed by the container 1 and the cover 2 in a fluid-tight manner.

Consequently, a vacuum is generated in the additional interior In2 in one embodiment. This vacuum acts from outside on the folded bag 3 and strives to pull the two overlap areas 3.1 and 3.2 of the folded bag 3 apart from one another, which overlap areas 3.1 and 3.2 are detachably connected to one another.

The device-side connector 11 is in fluidic connection with the collecting unit interior In1 in another embodiment. Air is suctioned out of the bag 3.

In both embodiments, a vacuum is generated in the bag 3. The detachable connection is severed because of this vacuum, and the bag 3 unfolds. The two overlap areas 3.1 and 3.2 unfold about the fold axis FA in this case. The unfolded bag 3 expands. The unfolded and expanded bag 3 is shown in FIG. 3.

Because of the vacuum in the bag 3, the secretion is suctioned into the collecting unit interior In1 through the patient-side fluidic connection, i.e., through the catheter 7, the suction tube 6 and the patient-side connector 4. The bag expands because of the vacuum and/or secretion. In many cases, the bag 3, which has unfolded because of the vacuum, clings from the inside to the inner wall of the container 1.

As soon as the bag 3 is filled up to a predefined maximum fill level or all secretion is suctioned out of the patient P, the suction tube 6 is removed from the patient-side connector 4. As a result, the suctioning is ended. The vacuum source 8 continues to be switched on. As a result, the bag 3 remains expanded.

The cap 3 is placed onto the patient-side connector 4 and prevents secretion from exiting from the expanded bag 3 through the cover 2.

The vacuum source 8 is now also switched off.

The collecting unit with the filled bag 3 is removed from the container 1 and is disposed of.

The device-side tube 17 remains on the device-side connector 11. The container 1 is able to receive a new collecting unit.

While specific embodiments of the invention have been shown and described in detail to illustrate the application of the principles of the invention, it will be understood that the invention may be embodied otherwise without departing from such principles.

LIST OF REFERENCE NUMBERS

1 Container, has the bottom 5, stands on the foot 18, accommodates the bag 3, carries the device-side connector 11, belongs to the collecting system
2 Cover for the container 1, carries the bag 3, accommodates the patient-side connector 4, belongs to the collecting unit
2.*a* Arched outer side of the cover 2
2.*i* Flat inner side of the cover 2, which inner side points towards the collecting unit interior In1
3 Expandable bag, receives secretion S from the patient P, held by the cover 2 in the interior of the container 1, comprises the overlap areas 3.1, 3.2 and the connection area 3.3, belongs to the collecting unit
3.1, 3.2 Overlap areas of the bag 3, which are overlapped when the bag 3 is folded and which are connected to one another in the connection areas VB.1 and VB.2, have the fold axis FA as common edge, pass over into the connection area 3.3
3.3 Connection area of the bag 3, between the overlap areas 3.1, 3.2 and the cover 2, extends around the projection 19
4 Patient-side connector, integrated into the cover 2, provides a passage between the outer side of the cover 2 and the collecting unit interior In1
5 Bottom of the container 1
6 Suction tube, belongs to the patient-side coupling unit, connected to the patient-side connector 4 and to the catheter 7
7 Catheter, connected to the suction tube 6, belongs to the patient-side coupling unit
8 Vacuum source, comprises a pump, connected to the device-side connector 11 via the device-side tube 17
9 Pressure difference measuring device which measures and displays the vacuum generated by the vacuum source 8
10 Optional filter between the device-side connector 11 and the vacuum source 8, arranged in the device-side tube 17
11 Device-side connector, arranged at the container 1, can be connected to the vacuum source 8 via the device-side tube 17
17 Device-side tube, connects the device-side connector 11 to the vacuum source 8
18 Foot, on which the container 1 stands
19 Circumferential projection on the inside of the cover 2, carries the bag 3, connected to the container 1
20 Cylindrical sintered filter, mounted on the inner side 2.*i* of the cover 2, protrudes into the bag 3
21 Grip at the cover 2
30 Cap for closing the patient-side connector 4
FS Joining point, at which the connection area VB.1 is pressed into the connection area VB.2
E.1 Corner of the overlap area 3.1, which the connection area VB.1 adjoins
E.2 Corner of the overlap area 3.2, which the connection area VB.2 adjoins
F Flow direction of secretion through the suction tube 6 into the bag 3
FA Fold axis of the bag 3, is at right angles to the cover 2 and to the bottom 5
In1 Collecting unit interior, formed by the interior of the bag 3 and by the flat inner side 2.*i* of the cover 2, is in fluidic connection with the device-side connector 11
P Patient, connected to the catheter 7
St Plunger of the tool W.1
VB.1, VB.2 Connection areas of the two overlap areas 3.1 and 3.2, have the corners E.1, E.2
W.1 First tool, comprises a plunger St
W.2 Second tool, comprises a corresponding receptacle, with which the plunger St meshes

What is claimed is:

1. A collecting unit for receiving secretion suctioned out of a patient, the collecting unit comprising:
a cover;
a bag mechanically connected to the cover, wherein:
the bag comprises at least one fold axis;

the bag and the cover together enclose a collecting unit interior for receiving secretion;

the bag is configured to be converted from a folded state, in which a portion of the bag is folded about the at least one fold axis, into an unfolded state, in which the bag is no longer folded about a fold axis;

the bag is configured such that in the folded state two overlapping overlap areas of the bag are formed and each of the two overlapping overlap areas have a connection area;

the two connection areas are detachably connected to one another;

the at least one fold axis forms a common edge of the two overlap areas;

the two connection areas are detachably connected to one another;

one of the two connection areas is at least partially wrapped around the other connection area or one of the two connection areas is pressed into the other connection area or one of the two connection areas is at least partially wrapped around the other connection area and one of the two connection areas is pressed into the other connection area.

2. A collecting unit in accordance with claim 1, wherein the bag has precisely one fold axis.

3. A collecting unit in accordance with claim 1, wherein the two connection areas are connected to one another with a pressed form fit connection.

4. A collecting unit in accordance with claim 1, wherein each connection area comprises a corner which is arranged at a spaced location from the cover and which is arranged at a spaced location from the at least one fold axis and which forms a corner of the bag.

5. A collecting device comprising:
a container; and
a collecting unit comprising:
a cover;
a bag mechanically connected to the cover, wherein:
the bag comprises at least one fold axis;
the bag and the cover together enclose a collecting unit interior for receiving secretion;
the bag is configured to be converted from a folded state, in which a portion of the bag is folded about the at least one fold axis, into an unfolded state, in which the bag is no longer folded about a fold axis;
the bag is configured such that in the folded state two overlapping overlap areas of the bag are formed and each of the two overlapping overlap areas have a connection area;
the two connection areas are detachably connected to one another;
the at least one fold axis forms a common edge of the two overlap areas;
the two connection areas are detachably connected to one another;
one of the two connection areas is at least partially wrapped around the other connection area or one of the two connection areas is pressed into the other connection area or one of the two connection areas is at least partially wrapped around the other connection area and one of the two connection areas is pressed into the other connection area;
the container carries the cover;
the bag is attached to the cover and protrudes into the container; and
the cover and the container together enclose a container interior.

6. A collecting device in accordance with claim 5, wherein:
the container has a bottom;
the container interior is located between the cover and the bottom; and
the bag reaches to the bottom both in the folded state and in the unfolded state.

7. A process for using a collecting unit comprising a cover, a bag mechanically connected to the cover, wherein the bag comprises at least one fold axis, the bag and the cover together enclose a collecting unit interior for receiving secretion, the bag is configured to be converted from a folded state, in which a portion of the bag is folded about the at least one fold axis, into an unfolded state, in which the bag is no longer folded about a fold axis, the bag is configured such that in the folded state two overlapping overlap areas of the bag are formed and each of the two overlapping overlap areas have a connection area, the two connection areas are detachably connected to one another, the at least one fold axis forms a common edge of the two overlap areas, the two connection areas are detachably connected to one another, and one of the two connection areas is at least partially wrapped around the other connection area or one of the two connection areas is pressed into the other connection area or one of the two connection areas is at least partially wrapped around the other connection area and one of the two connection areas is pressed into the other connection area, the process comprising the steps of:
detachably connecting the collecting unit to a container such that the bag protrudes into the container, wherein the bag is in the folded state and a portion of the bag is folded along the at least one fold axis and the cover and the container enclose a container interior, which comprises the collecting unit interior;
establishing a patient-side fluidic connection between a patient-side coupling unit and the collecting unit interior;
establishing a device-side fluidic connection between a vacuum source and the container, wherein:
the vacuum source generates a vacuum in the container interior;
the generated vacuum has the effect that the bag expands in the container interior;
the expansion causes the connection between the two overlap areas to be severed and the bag is converted into the unfolded state, and
secretion is suctioned into the bag through the patient-side fluidic connection.

* * * * *